United States Patent
Hagiwara

(10) Patent No.: US 6,366,088 B1
(45) Date of Patent: Apr. 2, 2002

(54) METHOD TO ENHANCE VERTICAL RESOLUTION OF TIME-DECAY LOG USING FORWARD MODELING DECONVOLUTION OF TIME-DECAY SPECTRA

(75) Inventor: Teruhiko Hagiwara, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 09/454,959

(22) Filed: Dec. 3, 1999

(51) Int. Cl.$^7$ .................................................. G01V 3/00
(52) U.S. Cl. ........................ 324/303; 324/338; 324/300
(58) Field of Search ................................. 324/338, 339, 324/309, 303, 300; 702/7

(56) References Cited

U.S. PATENT DOCUMENTS

| | | | |
|---|---|---|---|
| 5,144,245 A | * 9/1992 | Wisler | 324/338 |
| 5,184,079 A | * 2/1993 | Barber | 324/339 |
| 5,210,691 A | * 5/1993 | Freedman et al. | 364/422 |
| 5,666,057 A | * 9/1997 | Beard et al. | 324/339 |
| 5,867,806 A |   2/1999 | Strickland et al. | 702/7 |

* cited by examiner

*Primary Examiner*—Jay Patidar
*Assistant Examiner*—Brij B. Shrivastav
(74) *Attorney, Agent, or Firm*—Conley, Rose & Tayon, P.C.

(57) ABSTRACT

A method for enhancing measurement resolution is disclosed. In one embodiment, the method includes (1) obtaining multiple measurement samples at each of multiple positions along a borehole; (2) extracting reference index samples from the set of measurement samples; (3) determining a difference between each of the reference index samples and corresponding modeled index samples; and (4) updating a set of enhanced index samples based on the difference. The index samples are preferably chosen to be representative of the measurement samples obtained at each position, and accordingly, may be selected ones of the measurement samples, or alternatively, may be averages of the measurement samples. The aforementioned modeled index samples may be found from application of a predetermined tool response to the enhanced index samples, which in turn, may be found by iteration. Once the difference has been reduced below some threshold, the relationship between the enhanced index samples and the reference index samples may be used to calculate a deconvolution filter for all of the original measurement samples from the borehole. When applied to the original measurement samples, the deconvolution filter produces measurement samples having an enhanced resolution.

20 Claims, 3 Drawing Sheets

US 6,366,088 B1

METHOD TO ENHANCE VERTICAL RESOLUTION OF TIME-DECAY LOG USING FORWARD MODELING DECONVOLUTION OF TIME-DECAY SPECTRA

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The determination of whether a particular geological formation contains produceable hydrocarbon such as oil can be extraordinarily complicated. Initially, it must be determined what, if anything, a sub-surface formation contains. If it contains fluid, it must be determined whether this fluid is water, hydrocarbon, or both. It must then be determined whether it is cost effective to produce whatever hydrocarbons may be retrievable.

One difficulty encountered by the hydrocarbon industry is its need to retrieve a hydrocarbon stream from the ground that contains only a limited supply of water or brine. Thus, although an area may contain adequate hydrocarbons, excessive water may make it unsuitable for production. Resistivity tools have been useful in determining whether water is present in a hydrocarbon-rich formation. However, the mere presence of sub-surface water does not give a full picture of whether there exists producible hydrocarbon. This also depends upon the character of the detected water. Thus, resistivity tools are not ideal because they indicate merely the presence of water, and cannot indicate its mobility. When underground water comes up-hole with the retrievable hydrocarbons it is known as being free, movable, or reducible. Conversely, when the underground water remains down-hole at the time of production it is known as being bound, immovable, or irreducible. Thus, if one cannot determine the mobility of the underground water, many potentially productive hydrocarbon zones with high irreducible water saturation are bypassed because of fear of excessive water production.

One technology that has proved to be helpful in modern formation evaluation is nuclear magnetic resonance (NMR) technology. This technology assists in the control of water production and identification of pay zones with high irreducible (or bound) water saturation. One such NMR tool is the MRIL®, shown in FIG. 1. Also shown is a borehole 150. The MRIL® apparatus is a centralized device containing a permanent magnet and a radio frequency (RF) pulse generator (not shown). The tool as shown has an outer diameter 110 of 6" and a length of about 50'. A slim version of the tool (not shown) has an outer diameter of 4½". In an 8→ borehole 150, MRIL® depth of investigation 120 is 4 inches. The tool's permanent magnet generates a magnetic field of 2500 gauss (5,000 times the strength of the earth's magnetic field) with a field gradient of 17 gauss/centimeter. When random hydrogen nuclei interact with the applied magnetic fields, measurable signals are produced. The primary field of the permanent magnet aligns the hydrogen nuclei in one direction. The tool then uses its radio frequency generator to pulse a second magnetic field perpendicular to the permanent magnet's primary field. This RF generator operates at the Larmor frequency to rotate the nuclei 90° with respect to the alignment induced by the permanent magnet. After the RF pulse is turned off, the nuclei gradually dephase or disorder, causing the signal to decay exponentially. MILE operates on three close frequencies, which improves the signal to noise ratio and increases the logging speed. The exponential decay time constant for the dephasing of the nuclei is called the $T_2$ time, and the exponential time constant required for the nuclei to return to their initial aligned position is called the $T_1$, time. The $T_2$ time is shorter than the $T_1$ time and has been chosen as the time measured by the current MRIL® tool.

This $T_2$ time varies from one hydrogen nucleus to another, depending on the location of the hydrogen in the formation. When the hydrogen is located adjacent an underground rock surface, it comprises immovable or bound water. Surface tension holds this water to the rock surface and causes the water to remain downhole. When this bound fluid is affected by the magnetic field of an NMR tool, the rock causes the bound water to have a shorter $T_2$ time. Moveable water, in contrast, lives in the bulk, and not at the surface of a rock. Thus, the $T_2$ time of its hydrogen is unaffected by a rock's surface and so is longer in duration. In this way, movable water may be differentiated from immovable water based on their respective $T_2$ times.

One problem with the prior art NMR tools, in addition to many other tools such as the TMD (Thermal Neutron Decay) logging tool, is a limited vertical resolution. For example, because logging data may be sampled at ½ foot or ½ foot intervals, a common vertical resolution of about 10 inches would be desirable for all tools. However, the vertical resolution of the MRIL tool, for example, is only 2 to 4 feet. Therefore, the response of the tool may indicate only a single layer, when in reality, two or more layers exist in the measured region. The challenge is to establish the actual or "true" response at a specific depth when a tool yields a response that may encompass more than one layer of information.

Certain prior art methods exist to improve the vertical resolution of logging tools, but these methods are not directly applicable to tools such as the MRIL tool or any logging tool that is time, as well as depth, based. For example, improved resolution for an MRIL tool is particularly difficult because the tool must detect a changing value such as a hydrogen nuclei decay (or some other time-based measurement) at each depth rather than simply a "snapshot" value.

It is, therefore, not possible to resolve with sufficient accuracy multiple thin beds with a thickness less than the vertical resolution of the MRIL or TMD tool. Thus, present technology may not be able to adequately detect and measure thin beds that contain retrievable oil or other retrievable hydrocarbons. A tool or technique is needed to detect and measure these thin underground layers or beds. Ideally, this tool or technique could be used with most or all of the pre-existing oil field technology.

SUMMARY OF THE INVENTION

The above problems may advantageously be solved by a method for enhancing measurement resolution. In one embodiment, the method includes (1) obtaining multiple measurement samples at each of multiple positions along a borehole; (2) extracting reference index samples from the set of measurement samples; (3) determining a difference between each of the reference index samples and corresponding modeled index samples; and (4) updating a set of enhanced index samples based on the difference. The index samples are preferably chosen to be representative of the measurement samples obtained at each position, and accordingly, may be selected ones of the measurement samples, or alternatively, may be averages of the measurement samples. The aforementioned modeled index samples may be found from application of a predetermined tool response to the enhanced index samples, which in turn, may be found by iteration. Once the difference has been reduced below some threshold, the relationship between the enhanced index samples and the reference index samples may be used to calculate a deconvolution filter for all of the original measurement samples from the borehole. When applied to the original measurement samples, the deconvolution filter produces measurement samples having an enhanced resolution.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 1:
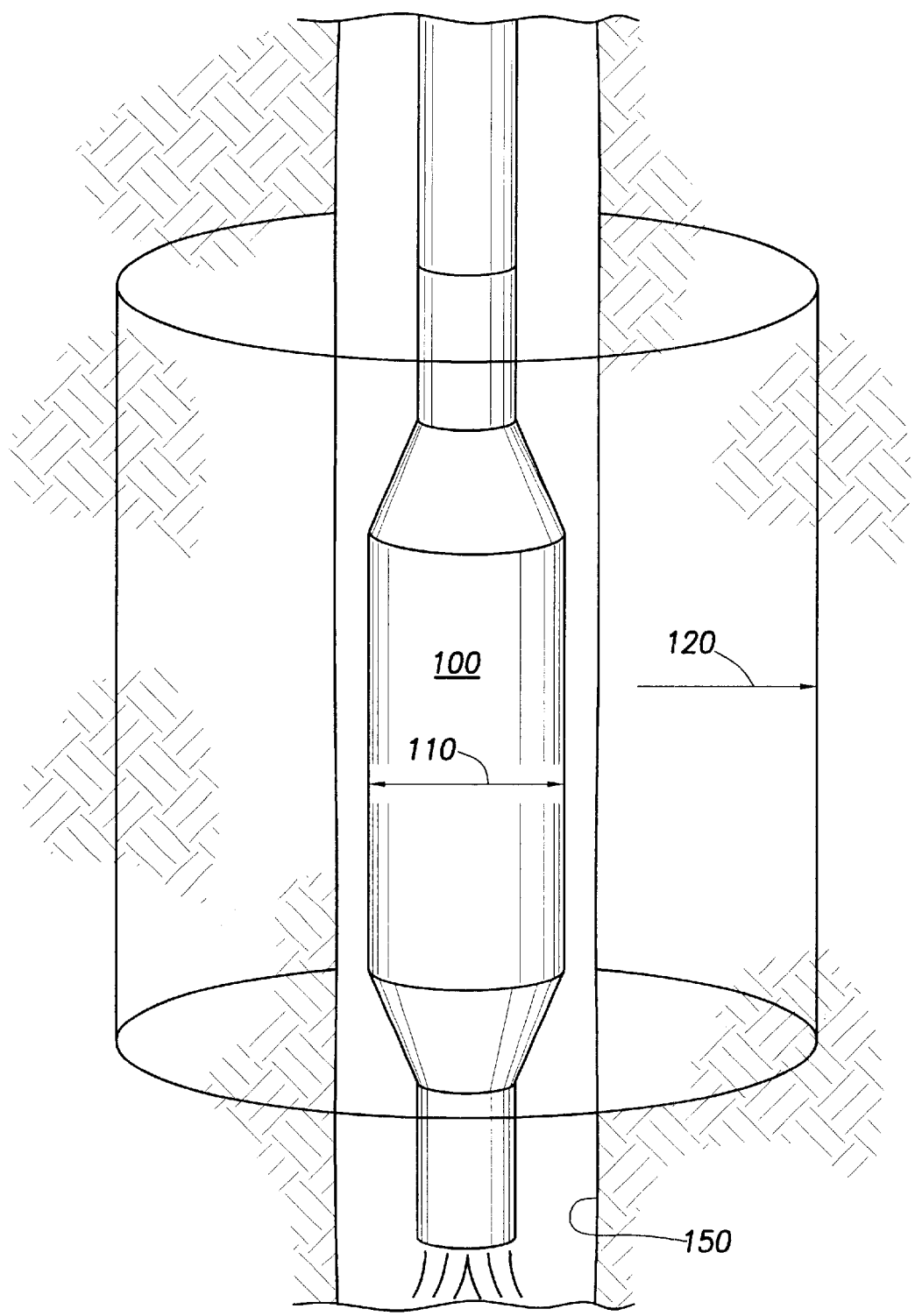
FIG. 1 is a diagram of an MRIL logging tool.

Logging tool response can be enhanced according to the preferred embodiment to produce data as if they were measured by a tool of finer resolution if it is known or assumed that there are a limited number of beds in the interval of the tool's resolution. In one of its forms, the invention is an improvement to the method disclosed in U.S. Pat. No. 5,867,806, the teachings of which are hereby incorporated by reference. Essentially, an iterative solution to finer vertical resolution may be obtained by use of a technique called inversion or forward modeling deconvolution. The types of tools of interest to the invention, however, measure not only a single piece of information at each logging depth, but, instead, measure an entire set of data at each logging depth.

Inversion is one technique that enhances tool resolution. In the inversion method of the preferred embodiment, MWD is performed to produce data logs. From the data logs an approximate or estimated model of the formation is made. This model of the formation essentially comprises an estimate of the characteristics of the formation. After the model of the formation is generated, a computer model of the tool response is used to transform the estimated model of the formation into an estimated log response. This estimated log response is then compared with the actual log data. One or more parameters of the model formation are then adjusted based on this comparison of the simulated log response to the actual log data, a new comparison is made, and the process repeats. Thus, the inversion technique iteratively refines the model formation until the simulated log matches the actual log. A corresponding forward modeling function or filter is then derived and may be applied to the measured data to derive the variable of interest.

To simplify the explanation of the invention, an NMR tool such as the MRIL will be used to illustrate the principles of the invention. In typical MWD, an NMR tool will measure the entire echo train at each depth. From these measured echo trains, a model is constructed in which hypothetical $T_2$ distributions may be assigned to the different layers of formation in the borehole. The depths of these layers can be determined by, for example, other tools measuring other characteristics, such as acoustic tools. Using the tool response, a hypothetical echo train may then be determined for any given depth. A series of these hypothetical echo trains is then compared with the series of measured echo trains at different depths and an error or degree of fit is established. The hypothetical $T_2$ distributions are iteratively adjusted until a reasonable degree of fit exists between the series of hypothetical echo trains and the series of measured echo trains. This yields the forward modeling filter.

To formalize the technique, $M(z,t)$ is used to represent the actual or true NMR echo train at a logging depth z. However, because of imperfections and shortcomings in a real world NMR tool, such as poor vertical resolution, the detected echo train at a particular depth z will be $M'(z,t)$. The detected echo train $M'(z,t)$ is related to the actual echo train $M(z,t)$ by the convolution equation:

$$M'(z,t) = \int f(z')M(z+z',t)dz' \tag{1}$$

Where, z=logging depth t=time $M'(z,t)$=detected echo train $M(z,t)$=true echo train $f(z)$=tool response function.

In terms of discrete data, this equation may be expressed as:

$$M'(z, t) = \sum_{i=-L}^{L} f(i)M(z + \delta z * i, t) \tag{2}$$

where the tool response function, $f(i)$, is non-zero between $z-L*\delta z$, and $z+L*\delta z$ as shown for example in FIG. 1. The tool response function for any particular design of tool will already be known.

A single or plural number of indices that correspond to (i.e., characterize) the entire detected data spectrum should then be chosen. For an NMR tool, such an index could be the T2 bin distribution, the FFI (free fluid index) value, the BVI (bound water volume index) value, or the total porosity. These indices are obtained by processing of the measured echo trains, and hence may be prone to noise-induced errors. Alternatively, selected points or ranges of the measured echo trains may be used directly as indices. To reduce noise, a weighted average of time samples within one or more time windows may be used to characterize the measured echo trains. Of course, the choice of index (or indices) may affect the usefulness of this resolution enhancement.

Figure 2:
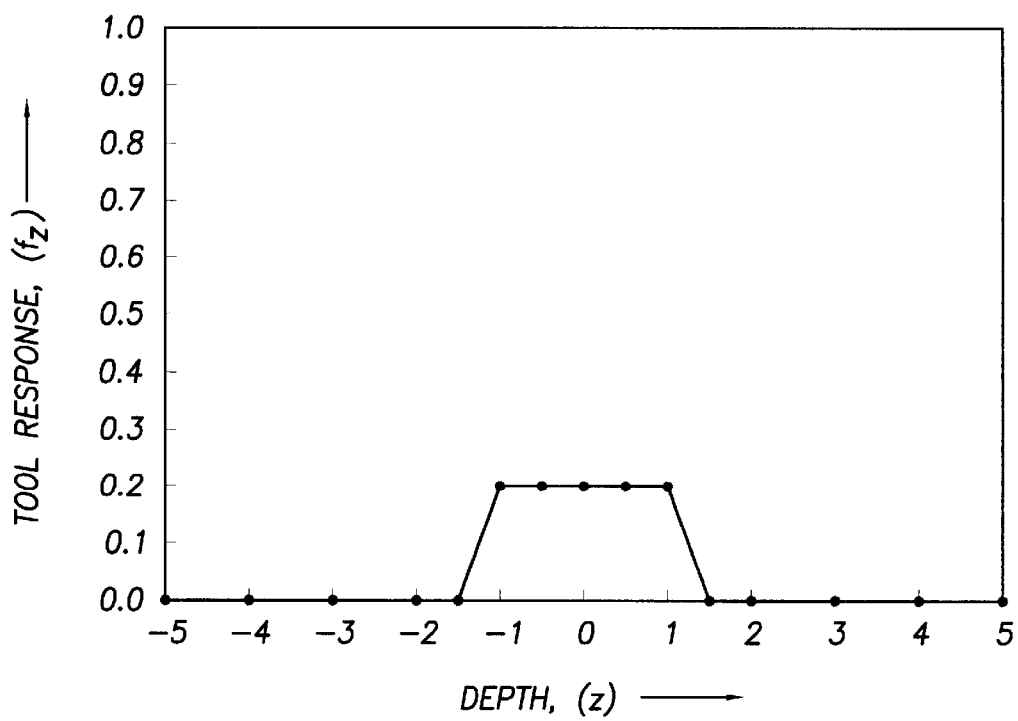
FIG. 2 shows a graph of a tool response function f(I).

The K selected indices for the measured echo trains $M'(z,t)$ are hereafter denoted as $I'^{K}(z)$. The ideal indices $I^{K}(z)$ for the actual echo train $M(z,t)$ can be determined from the measured indices. In one embodiment, the index values $I'^{K}(z)$ are the values of the measured echo train $M'(z,t)$ at times $t_K$. Since the selected index is linearly related to the amplitude of the echo trains, the relationship between the ideal and measured index values is given by:

$$I'^K(z) = \sum_{i=-L}^{L} f(i) I^K(z + \delta z * i), \quad (3)$$

where f(i) is the sampled tool response and $I'^K(z)$ is sampled at every $\delta z$ interval. This model is applicable so long as the tool motion is negligible during the time interval over which the time-decay spectrum is measured. In the case of an MRIL tool, the tool response function may appropriately be approximated as a constant over a 2-foot depth interval as shown in FIG. 2, if the tool resolution is 2 feet. This is also true with nuclear logging tool responses. To improve the vertical resolution of the tool, this $\delta z$ interval should be finer or smaller than the vertical resolution of the tool.

In an alternate embodiment, the selected indices may be the $T_2$-bin distribution calculated from the measured echo trains. In that case, the indices may be $I^K(z)=T_2(k,z)$.

One potential drawback to selecting the index values $I'^K(z)$ to be the values of the measured echo train M'(z,t) at times tK is the undesirable influence of measurement noise. This influence may be reduced by selecting the index values I'K(z) to be a straight average (or alternatively, a weighted average) of the values of the measured echo train M'(z,t) in a time window centered around the times $t_K$:

$$I'^K(z) = \sum_{i=-N}^{N} M'(z; t_K + \delta t * i) \quad (4)$$

Figure 3:
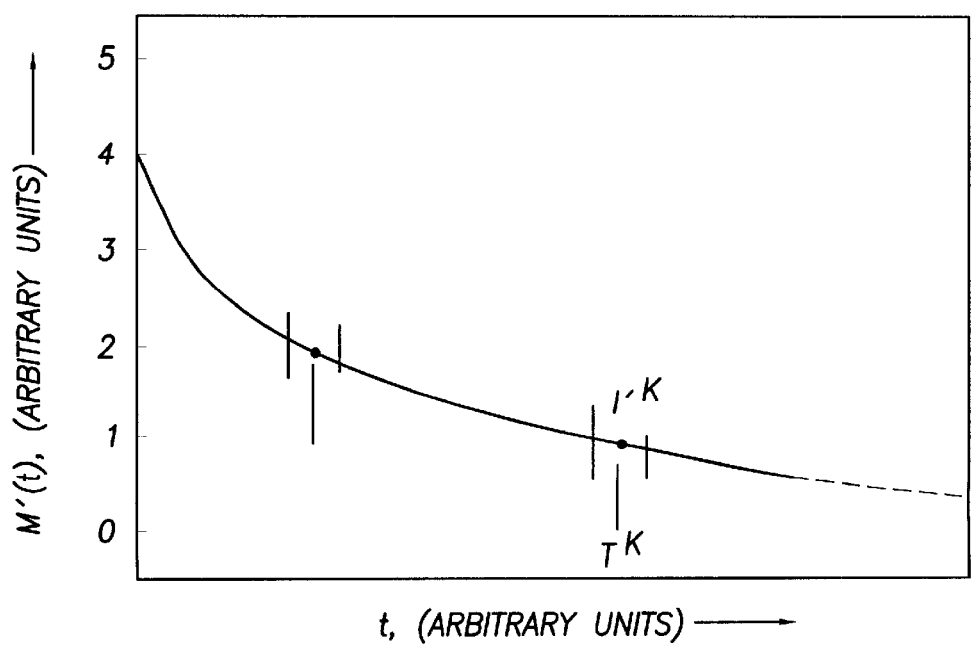
FIG. 3 shows a graph of interval time as applied to an NMR echo train.

The number of selected indices K may range from 1 at each sampled z position to the number to time samples at each sampled z position. In other words, the most complete set of indices is M'(z,t) itself. However, this may lead to an excessively heavy computational load, and consequently a subset of M'(z,t) may be used as the chosen index. A number of measured points is selected along the time-decay spectrum of the echo train, with a corresponding time window or gate around each point. For example, ten points, or more, or fewer, may be used. A graphic rendition of the interval time as applied to an echo train is shown in FIG. 3. Within each time window, an average is taken to find the index $I'^K(z)$.

Next, forward modeling deconvolution is applied to the $I'^K(z)$ data to estimate the ideal indices $I^K(z)$. The relationship between the ideal indices $I^K(z)$ and the measurement indices $I'^K(z)$ may be expressed by a forward deconvolution "filter" $g^K(z)$, defied by $$I^K(z)=g^K(z)I'^K(z) \quad (5)$$

Initially, neither the ideal indices nor the deconvolution filter is known. However, the iterative process explained below determines a model for the ideal indices which, when determined to be satisfactory, can be used to calculate the deconvolution filter coefficients.

The value of $g^K(z)$ can be derived from equation (4) for the ideal indices if a model ideal profile $I^K_{model}(z)$ is assumed. To determine if a model is satisfactory, the tool response f(i) is applied to the model ideal profile to determine a model measurement profile $I'^K_{model}(z)$ as follows:

$$I'^K_{model}(z) = \sum_{i=-L}^{L} f(i) I^K_{model}(z + \delta z * i) \quad (6)$$

Then $I'^K_{model}(z)$ is compared to the actual data $I'^K(z)$. The difference between the modeled response $I'^K_{model}(z)$ and the actual data $I'^K(z)$ is used to modify the model ideal profile on a point-by-point basis, similar to the way in which forward modeling is applied by those of ordinary skill in the art to "snapshot" data such as resistivity measurements. (See, e.g., U.S. Pat. No. 5,867,806, "System and method for performing inversion on LWD resistivity logs with enhanced resolution" issued to Robert Strickland, et al. on Feb. 2, 1999 and hereby incorporated herein by reference.) Because a number of modifications may be necessary to the model ideal profile before a better "fit" is achieved, this can be a computationally intensive approach. In any event, upon modification of the model ideal profile, the model measurement profile is again calculated. This process is repeated until sufficiently good agreement is achieved between the model measurement profile and the actual data. Then, the model ideal profile is regarded as the estimate of the true index $I^K_{est}(z)$.

A smoothed forward deconvolution filter g(z,t) may be generated from the set of $g^K(z)$ by noting the definition of $I'^K(z)$, $$I'^K(z) = \sum_{i=-N}^{N} M'(z; t_K + \delta t * i) \quad (7)$$

In other words, the deconvolution filter $g^K(z)$ can be processed to determine a deconvolution filter g(z,t) for application to the measured echo trains M'(z,t). The deconvolution filter coefficients $g^K(z)$ for a given echo train at location z may be repeated over and outside their time window centered at $t_K$, but they are preferably interpolated (using linear, polynomial, spline, or some other form of interpolation) in time to cover the maximum extent of the echo train at each location z. The forward modeling deconvolution of echo trains is then obtained by applying the smoothed filter g(z,t)

$$M_{est}(z,t)=g(z,t) M'(z,t) \quad (8)$$

Figure 4:
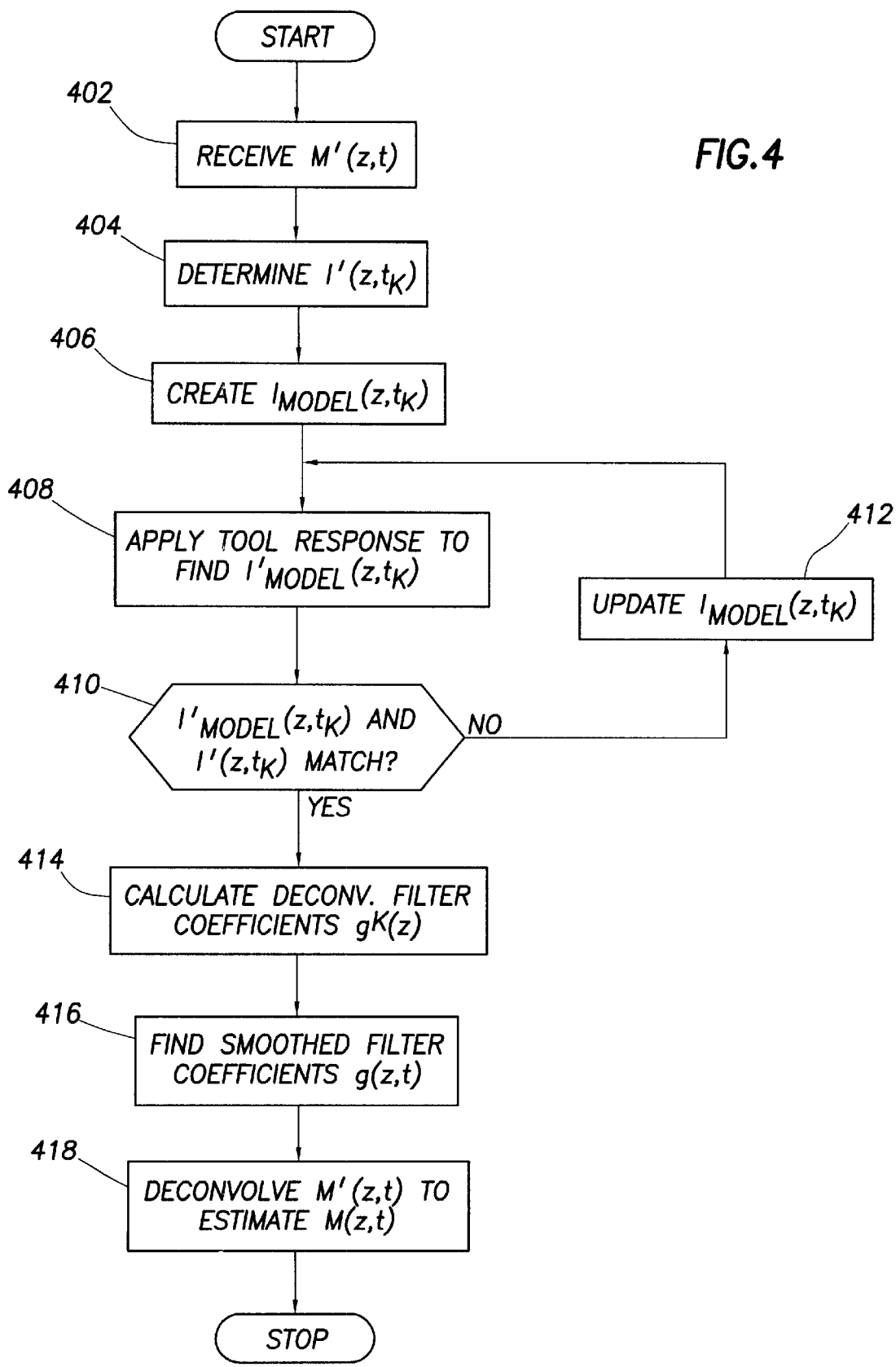
FIG. 4 shows a flow chart of the forward modeling deconvolution processing according to the preferred embodiment.

A flow chart of this forward modeling deconvolution processing is shown in FIG. 4. Although this explanation is made with reference to an NMR tool, it is equally applicable to other tools that obtain a set of data (such as based on time) at approximately a single depth. At step 402, a formation response such as an NMR echo train is measured downhole by the tool. At step 404, a set of measured indices is determined. At step 406, an initial set of model ideal indices is created. At step 408, the tool response is applied to the model ideal indices to find the corresponding model measurement indices. At step 410, a comparison of the model measurement indices is made with the actual measured indices. If the match is inadequate, the model ideal indices are updated at step 412. Otherwise, the deconvolution filter coefficients are calculated at step 414. In step 416, the smoothed filter coefficients are found, and at step 418, the smoothed filter is applied to the measured formation response to remove the effects of the tool response.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A method of processing time-decay logs to enhance vertical resolution, wherein the method comprises:
    retrieving a set of time-decay measurements measured at a plurality of positions;
    obtaining a plurality of actual measurement indices at each position from a time-decay measurement measured at that position;
    generating a plurality of initial model ideal indices at each position;
    applying a tool response to the model ideal indices to produce a plurality of model measurement indices;
    comparing the model measurement indices to the actual measurement indices to determine a difference; and
    updating the model ideal indices based on said difference.

2. The method of claim 1, wherein the actual measurement indices are the set of time-decay measurements.

3. The method of claim 1, wherein the actual measurement indices are T2-bin distribution values calculated from the set of time-decay measurements.

4. The method of claim 1, wherein the actual measurement indices are selected time samples from the set of time-decay measurements.

5. The method of claim 1, wherein the actual measurement indices are averages of time-decay measurements within selected time windows.

6. The method of claim 1, further comprising:
    repeating said applying, comparing, and updating steps to iteratively reduce the magnitude of said difference.

7. The method of claim 1, further comprising:
    calculating an index deconvolution filter from a ratio of the model ideal indices to the model measurement indices.

8. The method of claim 7, further comprising:
    smoothing the index deconvolution filter to produce a time-decay measurement deconvolution filter; and
    multiplying the set of time-decay measurements by the time-decay measurement deconvolution filter.

9. The method of claim 8, wherein said smoothing includes:
    setting time-decay measurement filter coefficients at a given position and at a given time sample equal to the index deconvolution filter coefficient closest in time at that position.

10. The method of claim 8, wherein said smoothing includes:
    interpolating the index deconvolution filter coefficients in time at a given position to calculate time-decay measurement filter coefficients for that position.

11. A method of enhancing measurement resolution, wherein the method comprises:
    obtaining a plurality of time-dependent measurement samples at each of a plurality of positions along a borehole;
    extracting a plurality of reference index samples for each of said plurality of positions from said plurality of time-dependent measurement samples;
    determining a difference between each of said plurality of reference index samples and a corresponding one of a plurality of modeled index samples; and
    updating a plurality of enhanced index samples based on said difference.

12. The method of claim 11, wherein said reference index samples are said plurality of time-dependent measurement samples.

13. The method of claim 11, wherein said reference index samples are selected measurement samples from said plurality of time-dependent measurement samples.

14. The method of claim 11, wherein said reference index samples are weighted averages of measurement samples associated with selected regions from said plurality of time-dependent measurement samples.

15. The method of claim 11, further comprising:
    generating said plurality of modeled index samples by application of a tool response to said updated plurality of enhanced index samples.

16. The method of claim 15, further comprising:
    repeating said determining, updating, and generating actions to iteratively reduce a magnitude of said difference.

17. The method of claim 11, further comprising:
    calculating a plurality of index deconvolution coefficients from a ratio of said enhanced index samples to said reference index samples.

18. The method of claim 17, further comprising:
    converting said plurality of index deconvolution coefficients into a plurality of measurement deconvolution coefficients; and
    multiplying said plurality of measurement samples by said plurality of measurement deconvolution coefficients.

19. The method of claim 18, wherein said converting includes:
    setting measurement deconvolution coefficients associated with a corresponding position and time equal to index deconvolution coefficients associated with an identical position and similar time.

20. The method of claim 18, wherein said converting includes:
    interpolating index deconvolution coefficients associated with a corresponding position to obtain measurement deconvolution coefficients associated with that position.

* * * * *